US011354937B2

(12) United States Patent
Invernizzi (10) Patent No.: US 11,354,937 B2
(45) Date of Patent: Jun. 7, 2022

(54) METHOD AND SYSTEM FOR IMPROVING THE VISUAL EXPLORATION OF AN IMAGE DURING A TARGET SEARCH (71) Applicant: SR Labs S.R.L., Brescia (IT)

(72) Inventor: Paolo Invernizzi, Milan (IT)

(73) Assignee: SR LABS S.R.L., Brescia (IT)

(*) Notice: Subject to any disclaimer, the term of this patent is extended or adjusted under 35 U.S.C. 154(b) by 697 days.

(21) Appl. No.: 14/390,544

(22) PCT Filed: Apr. 5, 2013

(86) PCT No.: PCT/IB2013/052730
§ 371 (c)(1),
(2) Date: Oct. 3, 2014

(87) PCT Pub. No.: WO2013/150494
PCT Pub. Date: Oct. 10, 2013

(65) Prior Publication Data
US 2021/0341997 A1 Nov. 4, 2021

(30) Foreign Application Priority Data

Apr. 5, 2012 (IT) .............................. FI2012A000072

(51) Int. Cl.
*G06V 40/18* (2022.01)
*G16H 40/63* (2018.01)
(Continued)

(52) U.S. Cl.
CPC .............. *G06V 40/18* (2022.01); *G06F 3/013* (2013.01); *G06F 3/0213* (2013.01);
(Continued)

(58) Field of Classification Search
CPC ...... G06F 3/013; G06F 3/0425; G06F 3/0213; G06F 3/017; G06V 40/18; G16H 30/40;
(Continued)

(56) References Cited

U.S. PATENT DOCUMENTS 8,020,993 B1 9/2011 Fram
2006/0215894 A1* 9/2006 Lakare .................. G16H 30/40
382/128

(Continued)

FOREIGN PATENT DOCUMENTS

WO 2006/128302 12/2006
WO WO-2006128302 A1 * 12/2006 ............. G06F 19/00

OTHER PUBLICATIONS

International Search Report and Written Opinion dated Sep. 23, 2013 for corresponding PCT patent application No. PCT/IB2013/052730.

Primary Examiner — Jonathan A Boyd
(74) Attorney, Agent, or Firm — Ableman, Frayne & Schwab (57) ABSTRACT Object of the present invention are a method and a system for monitoring a user's attention distribution in the course of a digital image exploration, adapted to produce feedback that give the user himself an indication of the efficacy of the exploration performed, even on the basis of the relevance that the various zones of the image have in relation to a certain goal, relevance that can possibly be determined by an expert system responsible for examining the image as a function of the above-mentioned objective.

12 Claims, 4 Drawing Sheets (51) Int. Cl.
*G16H 50/20* (2018.01)
*G16H 30/40* (2018.01)
*G06F 3/01* (2006.01)
*G06F 3/02* (2006.01)
*G06F 3/042* (2006.01)

(52) U.S. Cl.
CPC ........... *G06F 3/0425* (2013.01); *G16H 30/40* (2018.01); *G16H 40/63* (2018.01); *G16H 50/20* (2018.01)

(58) Field of Classification Search
CPC .......... G16H 40/63; G16H 50/20; G06T 7/73; G06T 2207/10016; G06T 2207/30201; A61B 6/463; A61B 6/467
See application file for complete search history.

(56) References Cited

U.S. PATENT DOCUMENTS

| | | | |
|---|---|---|---|
| 2007/0211930 A1* | 9/2007 | Dolwick | G06T 5/008 382/132 |
| 2008/0044068 A1 | 2/2008 | Evertsz | |
| 2011/0206283 A1 | 8/2011 | Quarfordt | |
| 2011/0307216 A1* | 12/2011 | Lindquist | G02B 27/0093 702/182 |

* cited by examiner

METHOD AND SYSTEM FOR IMPROVING THE VISUAL EXPLORATION OF AN IMAGE DURING A TARGET SEARCH

CROSS REFERENCE TO RELATED APPLICATIONS

This application is a national phase of PCT application No. PCT/IB2013/052730, filed Apr. 5, 2013, which claims priority to IT patent application No. FI2012A000072, filed Apr. 5, 2012, all of which are incorporated herein by reference thereto.

FIELD OF THE INVENTION

The present invention relates to the field of systems and methods for displaying images and adapted to assist users in reading and in using these images, with particular reference to the detection and identification of anomalies that said images have, with respect to reference images.

These systems have the task of helping the operator to improve the evaluation of the examined image and implement techniques and steps that allow the user to significantly reduce the cognitive effort needed and the research times to be used for examination of the image.

STATE OF THE ART

Various science and research fields employ image evaluation and analysis techniques wherein the detection and the classification of certain recognizable characteristics is the primary objective.

For example, medical imaging technologies produce various types of diagnostic images that the doctor or the radiologist can examine to search for the presence of specific identifiable characteristics and having diagnostic significance.

In the same way, in other fields, other characteristics may be of interest such as for example the analysis of satellite data and of meteorological radar that may aim to determine dangerous atmospheric phenomena, such as tornadoes or hurricanes, which prove to be in the initial formation phase in the analysed images. It is analogously possible to evaluate astronomical and geological images with analogous purposes identification purposes of particular characteristics which are difficult to detect.

In recent years, with the development of "digital imaging" techniques and of the related digital imaging processing techniques, the amount of images that can be advantageously subjected to exploration and analysis has increased considerably. New techniques have been developed as an aid to said digital imaging exploration and analysis of digital images, which can provide a first analysis of the data contained in the image in question, indicating the areas of interest for subsequent review by a person skilled in the art.

For example, in the field of medical diagnostic imaging there have been developed assisted detection and diagnosis algorithms (indicated with the acronym CAD, Computer Aided Diagnosis), adapted to integrate and help radiologists in reviewing the diagnostic images. Said algorithms are a valuable aid in the analysis of the images themselves, especially as regards the time needed to carry out said analysis, which must be optimised to achieve efficiency values such as to allow the prompt issue of diagnoses.

The so-called CAD systems are typically employed in the initial phase of the diagnostic process, to analyse the image and to highlight the regions of interest to prepare the further examination subsequently carried out subsequently by a by a person skilled in the art.

Since both the data and the results can have a high degree of complexity, it can be appropriate to operate a certain simplification thereof so as to focus the operator's attention on the characteristics of the image under observation that are deemed important. This is especially desirable in situations such as medical diagnosis where the amount of time spent on analysis by a person skilled in the art can delay the diagnosis and therefore the treatment, and where, partly due to the high degree of specialisation of the medical staff, there is really little time to analyse test results, often consisting of the series of many images.

There is currently no consolidated marker presentation technique to direct the operator's gaze onto the interesting area since each area requires a different presentation and display.

For example, in the medical radiology filed, the operator often prefers to analyse images that have a shape that is as faithful as possible to the original, so that the evaluation is not distorted by artefacts introduced by image processing techniques.

In the analysis of satellite images, on the other hand, the operator may be interested in highlighting the zone of interest by modifying certain image parameters such as contrast and brightness.

The prior art comprises various improvement and conditioning techniques of the image, which are adapted to facilitating the operator called to analyse the images in their search for particular information.

Patent applications U.S. 2007211930 and U.S. 2002054697 describe techniques based on the placing of markers on the image to be analysed and adapted to highlight the regions of interest by means of appropriate display techniques implemented in fixed and non-dynamic mode i.e. through the superimposition of static overlays on the image analysed by the user.

Patent application U.S. 2004100476 introduces an image display technique, which through the use of a visual aid tool, helps the operator to analyse the image emphasising and highlighting certain zones of interest through the direct and voluntary control exercised by the operator himself leaving the non-highlighted zones of the image visible.

Patent application U.S. 2006215894 describes an invention that employs eye-tracking systems to calculate, in particular, the time spent by the operator to review the markers placed by the CAD algorithm. In this case, the regions already analysed are indicated by a special marker. The list of markers used is fixed and the display thereof, again takes place in fixed and non-dynamic mode. The algorithm described in U.S. 2006215894 is divided into 2 successive steps and there is no possibility of providing feedback to the user.

Patent application U.S. 2006/0215894 concerns a method for displaying markers on a digital image, said markers being subdivided into two different sets, the first set produced in the course of a first scan of the image by the operator, the second produced by the CAD algorithm on the basis of said first scan. The combination and the comparison of these two sets of markers provide information and guidelines for the operator for the subsequent scans of the image.

Patent application U.S. 2011/0206283 discloses a method for monitoring a user's attention distribution in the course of the exploration of an image that provides for the on-screen display of the modifications of the image itself, adapted to direct the user's attention towards insufficiently analysed zones, while proposing them for a second analysis. The method described in U.S. 2011/0206283 is divided into two successive steps, following a first free exploration step on the part of the user, said image is repeated—whole or subdivided into blocks—so that only the previously unexplored parts are visible, so that the user examines the whole image. This occurs both in the case in which the unexplored regions are effectively relevant, and in the case in which they are not and the user purposefully wished to avoid them.

In one of the preferred embodiments described in patent application U.S. 2011/0206283, the areas already explored by the user appear represented as gaps in the image.

Techniques adapted to carry out a more in-depth analysis of the image to be analysed and of user behaviour during the scanning of the above-mentioned image and suitable for using highlighter markers of the dynamic type that avoid changing the analysed image are not present in the current state of the art.

This is of great importance since in certain applications, such as for example in the radiology field, specialists prefer to avoid the introduction of modification to the image to be examined since the modifications could, in any case, interfere with the analysis.

One aim of the present invention is therefore of method for monitoring a user's attention distribution in the course of the exploration of an image, adapted to produce feedback that give the user an indication of the efficacy of the exploration conducted even on the basis of the relevance that the various zones of the image have in relation to a certain objective.

Another aim of the present invention is a monitoring method of a user's attention distribution in the course of the exploration of an image, adapted to interface with an expert system responsible for preliminarily examining the image as a function of a certain objective to be identified.

A further aim of the present invention is a monitoring method of a user's attention distribution in the course of the exploration of an image, adapted not to modify the original image while also having dynamic and temporary visual stimuli, on the original image, aimed at attracting the user's attention towards a particular target deemed of interest by a potential expert system used. The feedback product will be adapted to lead the operator to view the target deemed of interest, to then dissolve so as to allow a clear view of the original image.

In addition, a further aim of the present invention is a monitoring method of a user's attention distribution in the course of the exploration of an image, adapted to suggest a so-called "optimal scanpath" to the user, i.e. the best image exploration strategy in relation to a certain objective, focusing the operator's attention on the points having higher relevance—according to the possible expert system responsible for preliminarily examining the image as a function of a certain objective to be identified—in order to maximise the image scanning efficiency on the part of the operator in the limited amount of time normally available for the above-mentioned scan.

SUMMARY OF THE INVENTION

Object of the present invention are a method and a system for monitoring a user's attention distribution in the course of the exploration of an image, adapted to produce feedback that give the user himself an indication of the efficacy of the exploration carried out, even on the basis of the relevance of the various image zones in relation to a certain objective, relevance that can possibly be determined by an expert system responsible for examining the image as a function of the above-mentioned objective.

Unlike the solutions of the prior art, the main characteristics of the method and the system according to the present invention are the following: a first feedback provided to the digital image analysis expert system possibly part of the system according to the present invention, adapted to update and modify the behaviour thereof on the basis of operator choices (self-learning); a second feedback comprising the dynamic placement of the highlighter markers on the digital image being examined; a single exploratory action having two steps: a first free exploration step and a subsequent second step wherein the system, automatically and also "learning" from the choices made by the user himself, guides the user in the search for the target through appropriate visual feedback.

In greater detail, the method and the system according to the present invention are adapted to identify the information relating to the observed and unobserved areas of the examined image, using the incoming information from the eye-tracking device, which monitors user gaze in real time and effectively communicates said information to the user himself.

The algorithm at the basis of the method according to the present invention is adapted to receive real-time information on the zones observed and not observed by the user, and to present at a suitable time (for example, when the operator is looking at a point deemed interesting but is going beyond) appropriate feedback that direct the user's attention to a certain zone of the image and then dissolve to allow display of the original image without any superimposed artefact.

In addition, the method and the system according to the present invention, allow the best view of the examined image to be presented to the user, by selecting the method deemed most effective for presenting the visual feedback to the user.

DETAILED DESCRIPTION OF THE INVENTION

Figure 1:
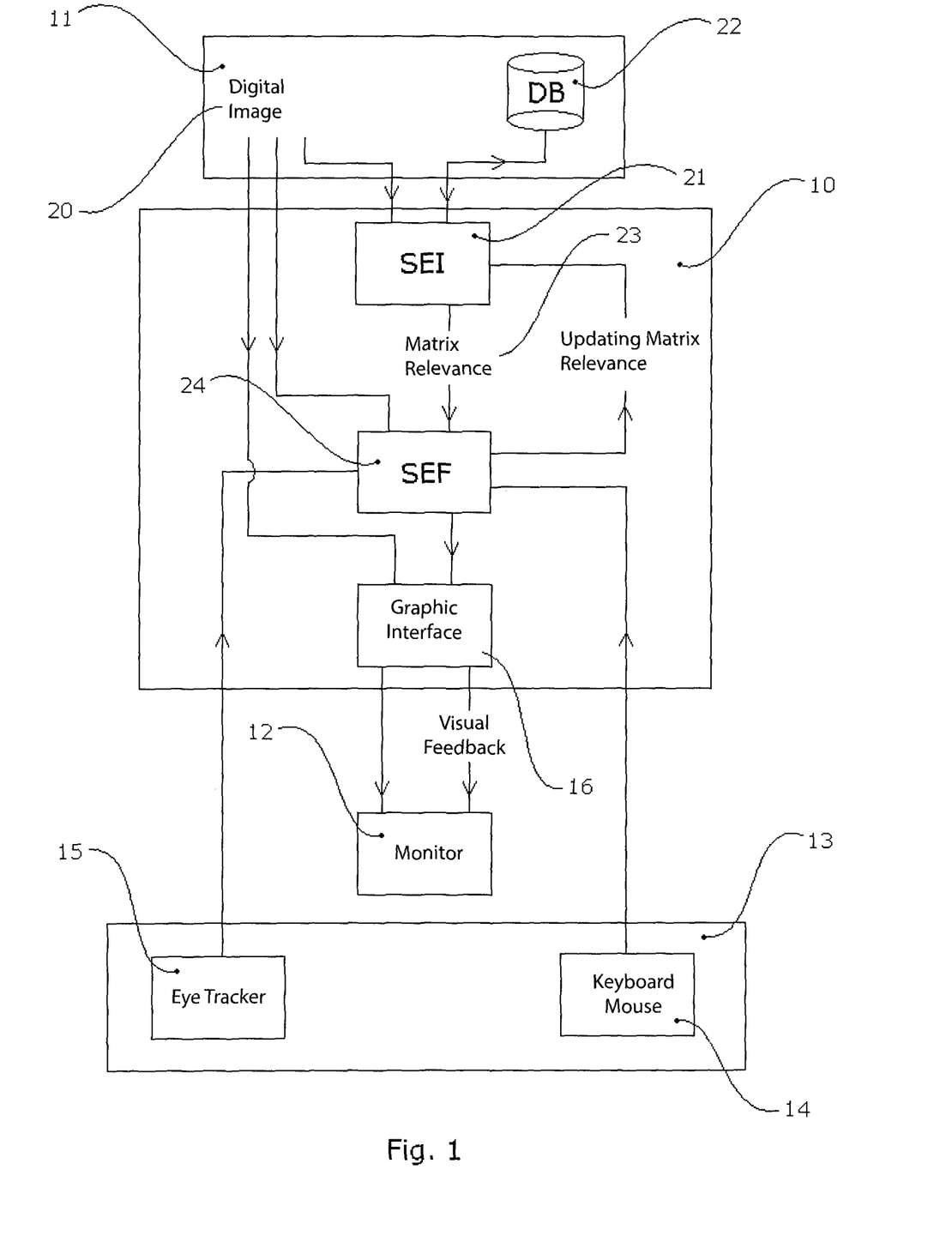
FIG. 1 shows the block diagram of the architecture of the method according to the present invention in the case in which the expert system responsible for preliminarily examining the image as a function of a certain objective to be identified is updated and a visual feedback is also provided to the user.

FIG. 1 illustrates an overview of the system according to the present invention comprising electronic data processing means 10, associated to data storage means 11, digital image display means 12 and interface means 13, adapted to allow said electronic data processing means to collect data from a user, wherein said electronic data processing means 10 are adapted, among other things, to modify the display of said digital images during the exploration thereof by the user so as to add indicators adapted to mark the zones of said digital images deemed important and which have not yet been explored by the user with the necessary care.

Said data processing means 10 can be implemented from any system able to perform calculations on the basis of a set of instructions contained in suitable data storage means. Said data processing means 10 can thus include personal computers, workstations, etc.

Said interface means 13 preferably comprise alphanumeric keyboards, mouse pointers, buttons 14 and eye-tracker devices 15.

A digital image 20, object of user analysis, is initially analysed by a first processing module comprising a first digital image analysis expert system 21 possibly but not necessarily stored in said data storage means 11 and adapted to establish a series of points of the same image deemed to be relevant as a function of a specific predefined target. Said first digital image analysis expert system 21 is adapted to interact with appropriate data bases 22 wherein are archived the results previously achieved in similar analyses, so that said first expert system 21 may progressively refine the accuracy of his detections.

The series of points identified by said expert system is generally organised according to a matrix, known as "relevance matrix" 23, wherein each point of the image is evaluated by means of a relevance index (with value between 0, no relevance, and 1, absolute relevance) with respect to the afore-mentioned default target.

At this point, said relevance matrix is provided, together with said image 20 and with the data originating from said interface means 13, at a second processing module comprising a second digital image analysis expert system 24, adapted to provide a feedback to both said first digital image analysis expert system 21 and to said digital image display means 12, preferably in the form of highlighter markers adapted to direct the user's attention to a certain zone of said image 20. Advantageously, said highlighter markers are adapted to dissolve after a certain interval of time so as to allow the user to view the original image without any permanent superimposed artefact.

Figure 3:
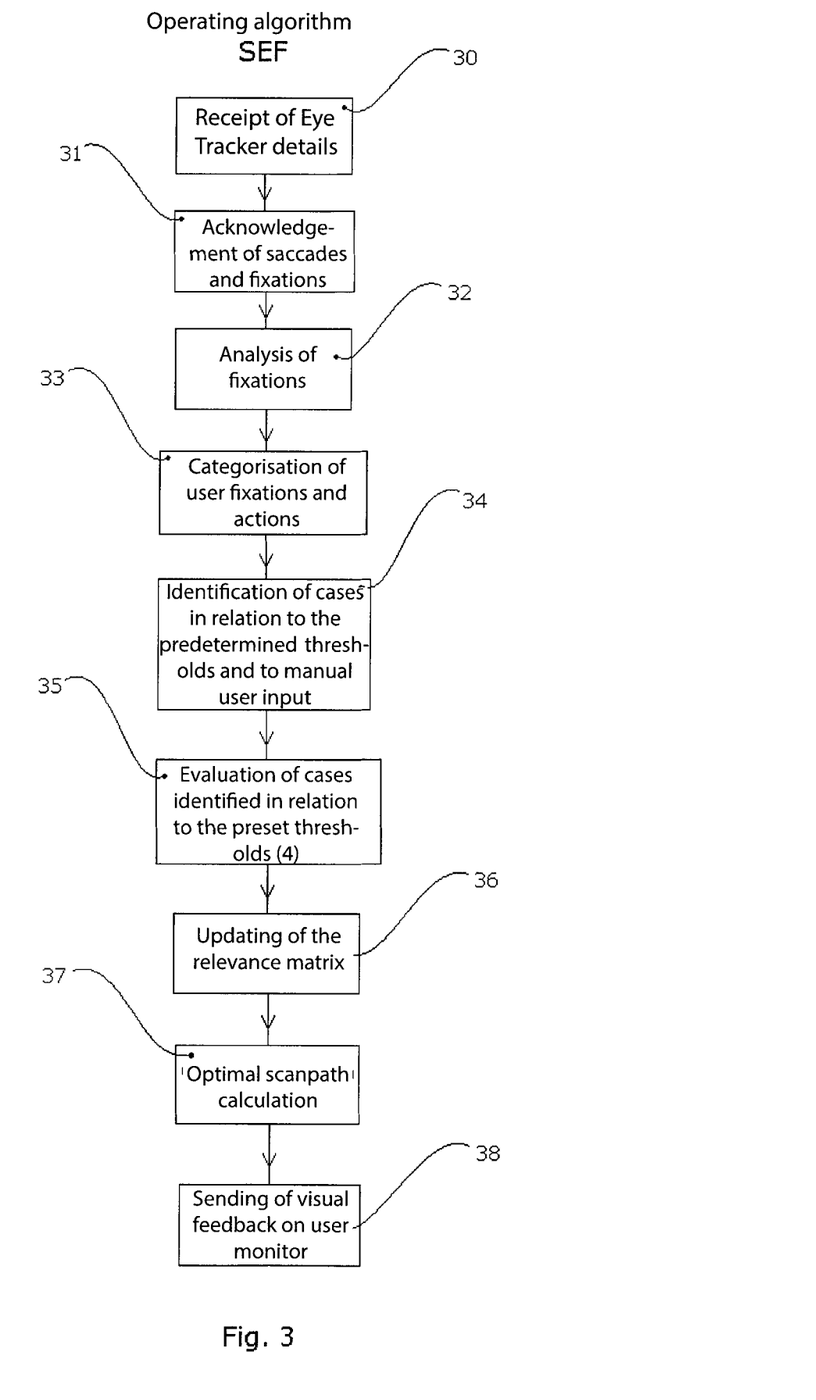
FIG. 3 shows a block diagram of the algorithm at the basis of the method according to the present invention.

In greater detail, and in reference to the accompanying FIG. 3, said second digital image analysis expert system 24 operates in the following way: the gaze of the user in the act of exploring said image 20 displayed on said digital image display means 12, is detected by said eye-tracker device 15 which, subsequently transmits 30 the collected data, relating to the gaze of the user, to said second digital image analysis expert system 24 which processes the data received so as to distinguish 31 the user's saccades from fixations. Said fixations are subsequently analysed 32 and categorised 33 in a certain number of cases 34 that are distinguished 35 in relation to some preset thresholds and relating to the relevance indexes of said relevance matrix. As a result thereof, the indexes of the relevance matrix are updated 36 by means of an updating of the training set of said first digital image analysis expert system 21 (for example, in the case of a neural network based expert system the parameters of the neural network are updated) and an optimal scanpath is calculated 37 on the basis of which dynamic markers are generated that are sent 38 to the graphic interface 16 of said data processing means 10 so as to be dynamically superimposed on said image 20, in such a way as to guide the user's attention towards the parts of the image deemed important and not yet adequately explored.

Said dynamic markers can be implemented, for example, with some zones with contrasting colours, with moving shapes adapted to attract the user's attention towards the zones of interest, with some simple direction indicators (arrows for example) pointing towards the zones of interest, or further still through zones which intermittently flash.

Advantageously, said highlighter markers are such as to dissolve after a certain interval of time so as to allow display of the original image without any superimposed modification.

The system object of the present invention can have different modes of operation, for example, it can operate in both the so-called active visual exploration mode (AVE, shown in FIG. 1 attached), in which overlap to the picture being examined highlighter markers described above according to the above described method, which in so-called mode of visual navigation passive (PVE, shown in FIG. 2 attached), in which do not overlap the image under examination highlighter markers described above, the exploration of the image 20 by the user, in this case is free and the system provides only to update the relevance matrix on the basis of the behaviour of the same user during the exploration of the image.

Figure 2:
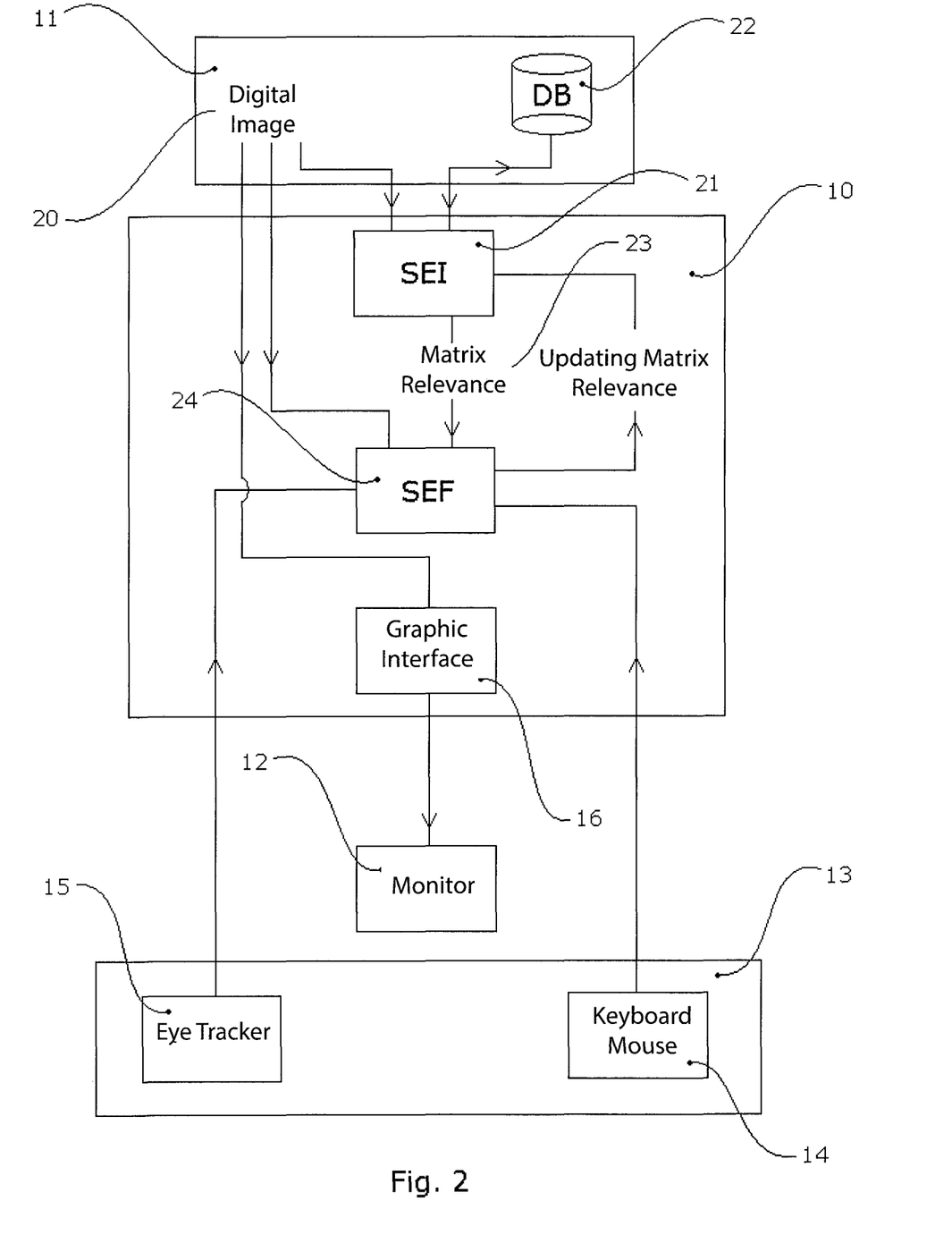
FIG. 2 shows the block diagram of the architecture of the method according to the present invention in the case in which the expert system responsible for preliminarily examining the image as a function of a certain objective to be identified is updated and no visual feedback is provided to the user.

A further mode of operation can provide for the alternation of the above-mentioned AVE and PVE modes. For example, the system object of the present invention can be set so as to acquire the image in question and operate for a certain initial time interval T1 in PVE mode up to the time in which the user displays the image and begins his exploration and, consequently, the system object of the present invention switches to AVE mode.

Figure 4:
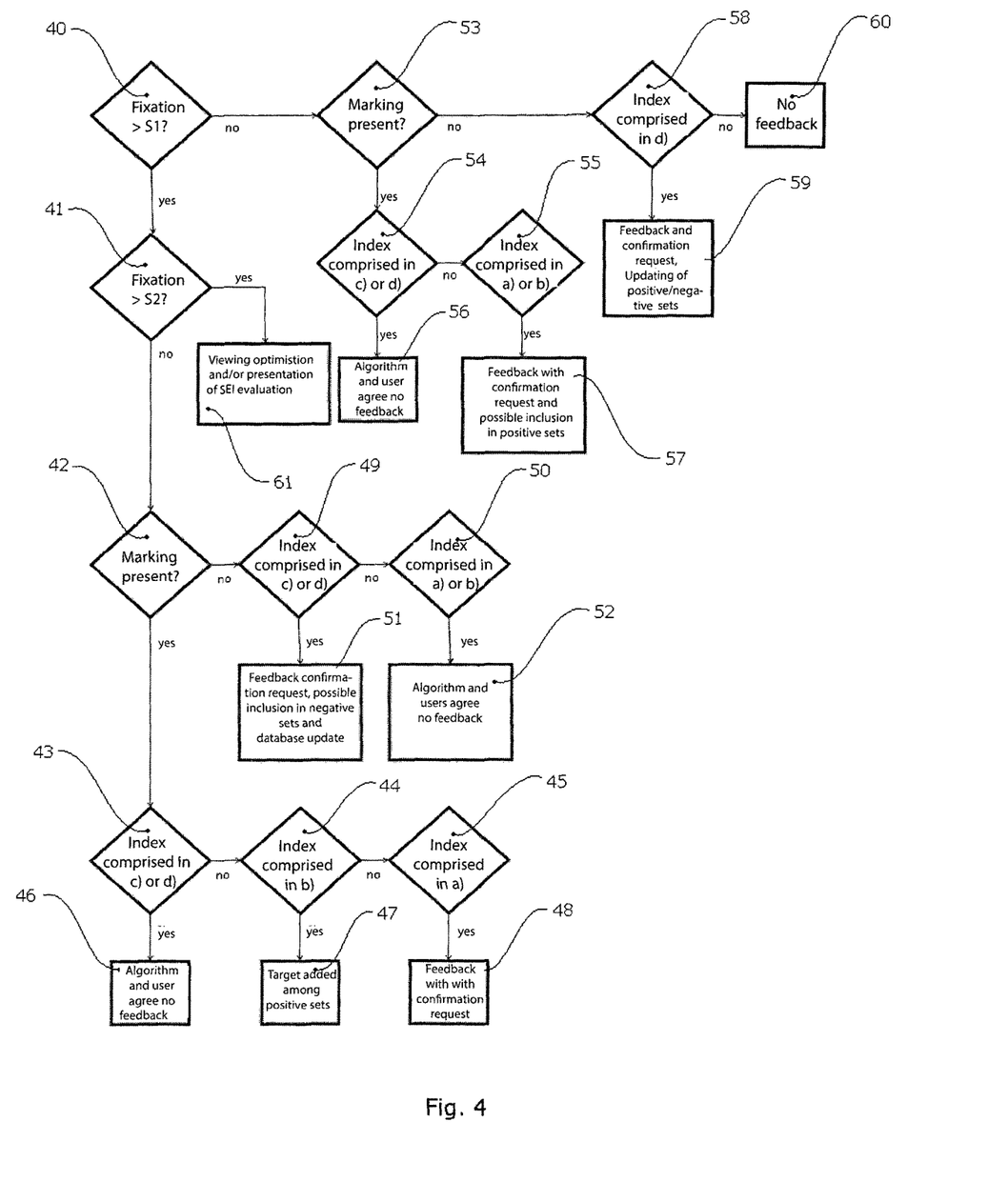
FIG. 4 shows the flow chart of the evaluation algorithm for user behaviour and the generation of the expert system update and of the feedback to display to the user.

In reference to the accompanying FIG. 4, an example of algorithm implemented in said second digital image analysis expert system 24 comprises the series of steps described below.

A certain number of distinction thresholds and ranges is established with respect to the possible values of said relevance index, for example, four distinction thresholds are established by dividing the range of values comprised between 0 and 1 into four sub-ranges: a) for relevance indexes between 0 and 0.2 (certain non-relevance of the observed point), b) between 0.2 and 0.5 (low probability of relevance of the observed point), c) between 0.5 and 0.8 (high probability of relevance of the observed point), d) between 0.8 to 1 (certain relevance of the observed point).

At this point, the data collected by said interface means 13 and relevant to the detection of the ocular movements of the user—by means of said Eye Tracker device 15 and the input provided by the user through said manual interface means 14—are processed in the following manner:

The point fixed by the user and the type of fixation (gaze) acquired with regards to two time thresholds, a first threshold S1 and a second threshold S2>S1, is evaluated 40, 41.

In the case that said fixation has a greater duration than both said first threshold S1 and said second threshold S2, the display of said digital image 20 is optimised 61 to promote the user's inspection thereof, possibly by displaying the current relevance index of the fixed points. Said optimisation can provide for an increase of the contrast, increase of the resolution, an increase of the zoom level, etc.

In the case of said fixation having a greater duration than said first threshold S1 but lesser than said second threshold S2, the presence of a manual input by the user (manual input corresponding to the user's intention to mark the point in question as important), is checked 42.

In the case of said manual input being present, the relevance index is compared 43, 44, 45 with said distinction thresholds; if said index belongs to said range of c) or to said range d), then the user agrees with said first digital image analysis expert system 21 and consequently said second digital image analysis expert system 24 does not produce 46 any feedback; if said index belongs to said range b) then the point set by the user between the points of interest of said image is added 47 by updating the set of positive targets; if said index belongs to said range a) then a graphic type feedback is provided 48 by means of a dynamic marker superimposed on the display of said digital image, possibly with user confirmation request.

In the case, on the other hand, in which said manual user input is not present, the relevance index is again compared 49, 50 with said distinction thresholds; if said index belongs to said range c) or to said range d), then there is generated a feedback adapted to insert 51, possibly with a user confirmation request, the point fixed by the user between the points of no interest of said image; if said index belongs to said ranges a) or b) then the user agrees with the first digital image analysis expert system 21 and consequently said second digital image analysis expert system 24 does not produce 52 any feedback.

In the case in which said fixation has a lesser duration than said first threshold S1, the presence of manual user input (manual input corresponding to the user's intention to mark the point in question as important) is again checked 53.

In the case of the presence of said manual input, the relevance index is compared 54, 55 with said distinction thresholds: if said index belongs to said range c) or to said range d), then the user agrees with said first digital image analysis expert system 21 and consequently said second digital image analysis expert system 24 does not produce 56 any feedback; if said index, on the other hand, belongs to the ranges a) or b), then a feedback is generated that is adapted to update 57, possibly with user confirmation request, the set of positive and negative so as to add the point of said digital image currently being examined to the set of positive points, while removing it from the set of negative points.

Lastly, in the case that said manual user input is not present, the relevance index is compared 58 with said distinction thresholds: if said index belongs to said range d), the algorithm is practically certain that the point in question is a positive target and user confirmation is requested 59: if the user agrees then it is confirmed that the point is a positive target, otherwise if the user does not agree, the point is removed from the set of positive targets and added to the set of negative targets. This is a case in which the point examined is a simple target of the negative type or a case in which the user has paid little attention during his analysis.

If, on the other hand, said index does not belong to the range d), no feedback is produced 60.

The invention claimed is:

1. A system for improving the analysis of digital images by a user comprising:
    electronic data processing means connected to a digital image analysis expert system associating a relevance index to the zones of said image, said data processing means comprising:
    a data storage device,
    a digital image display, and
    a user interface including an eye-tracker device, wherein said electronic data processing means is operable to:
    record visual interaction of the user with a digital image shown on the digital image display and compare said interaction with said relevance index;
    generate first feedback based on the visual interaction of the user with the eye-tracker device to update said relevance index;
    generate second feedback to provide dynamic markers adapted to highlight zones of said digital image that the user has interacted with which are in disagreement with said relevance index; and
    send said dynamic markers to said digital image display to be displayed superimposed on said digital image.

2. The system according to claim 1, wherein said user interface comprise devices selected from the group comprising: alphanumeric keyboards, mouse pointers and buttons and eye-tracker devices.

3. The system according to claim 1, wherein said electronic data processing means comprising data storage further comprise a first processing module having a first digital image analysis expert system adapted to interact with appropriate databases so as to associate a relevance index to each point of the analysed digital image as a function of a certain predetermined target, and a second processing module having a second digital image analysis expert system which is configured to supply a feedback to both said first digital image analysis expert system and to said digital image display means.

4. The system according to claim 3, wherein said feedback supplied to said first digital image analysis expert system comprises an update of the value of the relevance index associated to each point of said digital image.

5. The system according to claim 1, wherein said dynamic highlighter markers dissolve after a predetermined interval of time so as to allow display of the original image without any superimposed modification.

6. The system according to claim 1, wherein said dynamic highlighter markers are selected from the group comprising: zones of said image with contrasting colours, moving shapes superimposed on said image and adapted to attract the user's attention towards the zones of interest of said image, direction indicators facing towards the zones of interest of said image, and zones of said image which intermittently blink.

7. The system according to claim 3, wherein said second digital image analysis expert system is adapted to process the data received from said eye-tracker device so as to distinguish the user's saccades from fixations; to analyse and categorize said fixations into a certain number of cases which are distinguished in relation to predetermined thresholds and related to the relevance indexes of the points of said image fixed by the user; to update the value of the relevance index associated to each point of said digital image and to transmit said updated relevance index value to said first digital image analysis expert system; to calculate an optimal scanpath of said image; to generate dynamic markers, on the basis of said optimal scanpath, that are adapted to highlight appropriate zones of said image; to send said dynamic markers to said graphic interface of said data processing means so that they are appropriately superimposed on said image and suggest said optimal scanpath to the user.

8. A method for improving the analysis of digital images by a user comprising:
    displaying a digital image to a user on display means connected to data processing means in turn connected to storage means and user interface means comprising an eye-tracker device;
    acquiring the user's scanpath of said image by means of the eye-tracker device;
    checking the presence of user' s manual inputs to mark selected zones of the displayed image, if any;

comparing the user's scanpath of said image and the user' manual inputs to mark selected points of the displayed image, if any, to the relevance index of the zones points of said image, originating from a digital image analysis expert system:

generating a first feedback adapted to update said relevance index of the zones of said image, originating from a digital image analysis expert system, based on the comparison of the previous step;

generating a second feedback to create dynamic markers adapted to highlight zones of said image that the user has interacted with in disagreement with said relevance index;

sending said dynamic markers to said display means to be displayed superimposed on said image.

9. The method according to claim 8, wherein comparing the user's scanpath of said image and the user's manual inputs to mark selected points of the displayed image, if any, to said relevance index is carried out after establishing a number of time thresholds for the user' s gazing and a number of ranges with respect to said relevance index.

10. The method according to claim 8, wherein said first and second feedbacks are produced according to the following steps:

establishing four distinction ranges by dividing the range of values of said relevance index, comprised between 0 and 1, into four sub-ranges: a) for relevance indexes between 0 and 0.2, b) between 0.2 and 0.5, c) between 0.5 and 0.8, d) between 0.8 and 1; evaluating the point fixed by the user and the type of fixation acquired with regards to two time thresholds, a first threshold S1 and a second threshold S2>S1;

in the case that fixation has a greater duration than both said first threshold S1 and said second threshold S2, the display of said digital image is optimised to promote the user's inspection thereof; if said fixation has a longer duration than said first threshold S1 but lesser than said second threshold S2, checks for the presence of a manual input by the user corresponding to the user's intention to mark the concerned point as important are carried out, and if present the relevance index is compared with said distinction thresholds, if said index belongs to said range c) or to said range d), no feedback is produced, if said index belongs to said range b) feedback is produced by adding the point fixed by the user to the interest points of said image by updating the set of positive target points, if said index belongs to said range a) a graphic type feedback is provided by means of a dynamic marker superimposed on the display of said graphic image;

in the case that said manual input by the user is not present, the relevance index is compared with said distinction thresholds, if said index belongs to said range c) or to said range d), a feedback is generated that is adapted to insert the point fixed by the user into the points which are not of interest of said image, if said index belongs to said ranges a) or b), no feedback is produced;

in the case in which said fixation has a shorter duration than said first threshold S1, checks for the presence of manual input by the user are carried out, if present, the relevance index is compared with said distinction thresholds: if said index belongs to said range c) or to said range d), no feedback is produced, if said index belongs to said ranges a) or b), feedback is generated that is adapted to add the point of said digital image currently being examined to the set of positive points, removing it from the set of negative points;

in the case that said manual input by the user is not present, the relevance index is compared with said distinction thresholds: if said index belongs to said range d), user confirmation that the examined point is a positive target is requested: if the user agrees, then it is confirmed that the point is a positive target, otherwise, if the user does not confirm, the point is removed from the set of positive targets and added to the set of negative targets, if said index does not belong to said range d), no feedback is produced.

11. A non-transitory computer-readable recording medium having a program recorded thereon, said readable recording medium comprising computer program code means adapted to implement all the steps of claim 7, when said computer program is executed on the computer.

12. The method according to claim 8, wherein said second feedback is produced according to the following steps: establishing four distinction ranges by dividing the range of values of said relevance index, comprised between 0 and 1, into four sub ranges: a) for relevance indexes between 0 and 0.2, b) between 0.2 and 0.5, c) between 0.5 and 0.8, d) between 0.8 and 1; evaluating the point fixed by the user and the type of fixation acquired with regards to two time thresholds, a first threshold S1 and a second threshold S2>S1; in the case that fixation has a greater duration than both said first threshold S1 and said second threshold S2, the display of said digital image is optimised to promote the user's inspection thereof; if said fixation has a longer duration than said first threshold S1 but lesser than said second threshold S2, checks for the presence of a manual input b the user corresponding to the user's intention to mark the concerned point as important are carried out, and if present the relevance index is compared with said distinction thresholds, if said index belongs to said range c) or to said range d), no feedback is produced, if said index belongs to said range b) feedback is produced by adding the point fixed by the user to the interest points of said image by updating the set of positive target points, if said index belongs to said range a) a graphic type feedback is provided by means of a dynamic marker superimposed on the display of said graphic image in the case that said manual input by the user is not present, the relevance index is compared with said distinction thresholds, if said index belongs to said range c) or to said range d), feedback is generated that is adapted to insert the point fixed by the user into the points which are not of interest of said image, if said index belongs to said ranges a) or b), no feedback is produced; in the case in which said fixation has a shorter duration than said first threshold S1, checks for the presence of manual input by the user are carried out, if present, the relevance index is compared with said distinction thresholds: if said index belongs to said range c) or to said range di, no feedback is produced if said index belongs to said ranges a) or b), feedback is generated that is adapted to add the point of said digital image currently being examined to the set of positive points, removing it from the set of negative points; in the case that said manual input by the user is not present, the relevance index is compared with said distinction thresholds: if said index belongs to said range d), user confirmation that the examined point is a positive target is requested: if the user agrees, then it is confirmed that the point is a positive target, otherwise, if the user does not confirm; the point is removed from the set of positive targets and added to the set of negative targets, if said index does not belong to said range d), no feedback is produced.

* * * * *